United States Patent
Kempinski

(10) Patent No.: US 9,746,918 B2
(45) Date of Patent: Aug. 29, 2017

(54) EYE TRACKING

(71) Applicant: Umoove Services Ltd., Jerusalem (IL)

(72) Inventor: Yitzchak Kempinski, Geva Binyamin (IL)

(73) Assignee: Umoove Services Ltd., Jerusalem (IL)

( * ) Notice: Subject to any disclaimer, the term of this patent is extended or adjusted under 35 U.S.C. 154(b) by 0 days.

(21) Appl. No.: 14/373,906

(22) PCT Filed: Jan. 27, 2013

(86) PCT No.: PCT/IL2013/050072
§ 371 (c)(1),
(2) Date: Sep. 7, 2014

(87) PCT Pub. No.: WO2013/111140
PCT Pub. Date: Aug. 1, 2013

(65) Prior Publication Data
US 2015/0002392 A1 Jan. 1, 2015

Related U.S. Application Data

(60) Provisional application No. 61/590,905, filed on Jan. 26, 2012.

(51) Int. Cl.
| | |
|---|---|
| *G06F 3/01* | (2006.01) |
| *A61B 3/113* | (2006.01) |
| *G06K 9/00* | (2006.01) |
| *G06T 7/246* | (2017.01) |

(52) U.S. Cl.
CPC .............. *G06F 3/013* (2013.01); *A61B 3/113* (2013.01); *G06K 9/00604* (2013.01); *G06T 7/248* (2017.01); *G06T 2207/30041* (2013.01)

(58) Field of Classification Search
None
See application file for complete search history.

(56) References Cited

U.S. PATENT DOCUMENTS

| | | | |
|---|---|---|---|
| 6,421,064 B1 | 7/2002 | Lemelson et al. | |
| 7,130,453 B2 * | 10/2006 | Kondo | ............... G06K 9/00617 382/117 |
| 8,527,908 B2 | 9/2013 | Pance et al. | |
| 9,202,280 B2 * | 12/2015 | Wu | .......... G01S 17/06 |

(Continued)

FOREIGN PATENT DOCUMENTS

| | | |
|---|---|---|
| WO | WO 2011/066343 | 6/2011 |
| WO | WO 2012/038589 | 3/2012 |
| WO | WO 2013/168171 | 11/2013 |

OTHER PUBLICATIONS

International Search Report of PCT Application No. PCT/IL2013/050409 dated Sep. 12, 2013.

*Primary Examiner* — Joseph Haley
*Assistant Examiner* — Emily Frank
(74) *Attorney, Agent, or Firm* — Pearl Cohen Zedek Latzer Baratz LLP

(57) ABSTRACT

An eye tracking method includes: in a frame of a series of acquired frames, estimating an expected size and expected location of an image of an iris of an eye within that frame; and determining a location of the iris image within that frame by identifying a region within the expected location, the size of the region being consistent with the expected size, pixels of that region being darker than pixels of other such regions within that frame.

18 Claims, 5 Drawing Sheets

(56) References Cited

U.S. PATENT DOCUMENTS

| | | | |
|---|---|---|---|
| 2003/0169213 A1 | 9/2003 | Spero | |
| 2004/0005083 A1* | 1/2004 | Fujimura | A61B 3/113 382/103 |
| 2004/0161134 A1 | 8/2004 | Kawato | |
| 2004/0240709 A1* | 12/2004 | Shoemaker | G06F 3/013 382/103 |
| 2005/0243054 A1 | 11/2005 | Beymer et al. | |
| 2006/0110008 A1 | 5/2006 | Vertegaal et al. | |
| 2010/0183205 A1* | 7/2010 | Pfleger | A61B 5/16 382/128 |
| 2010/0303294 A1* | 12/2010 | Zschau | A61B 3/113 382/103 |
| 2011/0006978 A1 | 1/2011 | Yuan | |
| 2011/0317872 A1 | 12/2011 | Free | |

* cited by examiner

EYE TRACKING

CROSS-REFERENCE TO RELATED APPLICATIONS

This application is a National Phase Application of PCT International Application No. PCT/IL2013/050072, International Filing Date Jan. 27, 2013, claiming priority of U.S. Patent Application No. 61/590,905, filed Jan. 26, 2012, each of which being hereby incorporated by reference.

FIELD OF THE INVENTION

The present invention relates to tracking of eyes.

BACKGROUND OF THE INVENTION

Eye tracking is useful for some types of systems and devices. For example, a system may analyze an image of a human face in order to determine a gaze direction that indicates where the eyes are looking or for determining a position of the head. Tracking of the eyes may be utilized in various ways. In some systems, tracking of a gaze direction may be used to control a displayed image. For example, if it is determined from the gaze direction that a user is reading a portion of text at the edge of a display screen, the display system may automatically scroll the text so as to enable the user to continue reading the text without interruption or without manually manipulating controls. Similarly, a section of an image at which the user is looking may be automatically centered in the field of view. Display control by eye tracking may be especially useful in a handheld device with a relatively small screen, such as a smartphone, or when manual control is difficult or inadvisable.

Tracking an object may be made difficult by the varied appearance of the object in different situations. The appearance of the object may constantly change during tracking due to changes in apparent size due to changes in distance of the object from the tracking camera. Other properties of the object that may change during tracking may include real or apparent shape, perceived color (e.g. due to non-uniform coloring of the object as is changes orientation or due to changing lighting or illumination), and orientation. In the particular case of eyes, the appearance of eyes may be different from person to person. Differences in facial features from person to person or presence of glasses frames may also increase the difficulty of identifying or tracking eyes in an image of a face. A low quality image sensor may also contribute to difficulty in tracking.

Thus, accurately tracking an object in real time, especially of subtle eye movements, may impose severe demands on a camera or processor resources used in tracking the object.

SUMMARY OF THE INVENTION

There is thus provided, in accordance with embodiments of the present invention, an eye tracking method including: in a frame of a series of acquired frames, estimating an expected size and expected location of an image of an iris of an eye within the frame; and determining a location of the iris image within the frame by identifying a region within the expected location, a size of the region being consistent with the expected size, wherein pixels of the region have luminance values darker than pixels of other regions within the expected location.

Furthermore, in accordance with some embodiments of the present invention, the method includes calculating a luminance measure of a plurality of the pixels in the region, and comparing the measure to a measure of luminance of a plurality of pixels in other regions in the expected location.

Furthermore, in accordance with some embodiments of the present invention, estimating the expected size and the expected location includes applying a face detection algorithm to the frame.

Furthermore, in accordance with some embodiments of the present invention, estimating the expected location includes comparing a value associated with a template of pixels in a prior frame to each of a plurality of values, each of the plurality of values associated with a template of a plurality of templates of pixels in the frame, and identifying a location in the frame of a template of the plurality of templates whose associated value is closest to said value associated with the template of pixels in the prior frame.

Furthermore, in accordance with some embodiments of the present invention, the comparing includes calculating the value for the template of the plurality of templates by summing values of pixels in the template of the plurality of templates, the template of the plurality of templates including a number of pixels approximating a number of pixels in the template of pixels in the prior frame.

Furthermore, in accordance with some embodiments of the present invention, the method includes altering a location of the template of the plurality of templates, and adding to the summing only values of pixels included in the template by giving effect to the altering, and eliminating from the summing only values of pixels excluded from the template by giving effect to the altering.

Furthermore, in accordance with some embodiments of the present invention, the comparing includes calculating a sum of absolute differences between the value associated with the template of pixels in the prior frame to each of the plurality of values.

Furthermore, in accordance with some embodiments of the present invention, the method includes applying a non-linear manipulation to the values of pixels in the template of the plurality of templates by a pre-defined factor.

Furthermore, in accordance with some embodiments of the present invention, the estimating of the expected size includes comparing a distance in pixels between eyes of a face in the frame to a distance in pixels between eyes in a prior frame of the series of frames, and changing the size relative to a change in the distances.

Furthermore, in accordance with some embodiments of the present invention, the method includes increasing a luminance value of pixels in the expected location if the pixels have chrominance values above a threshold level.

There is further provided, in accordance with some embodiments of the present invention, an eye tracking device including: a camera, the camera configured to capture an image of a face in each frame of a series of frames; and a processor configured to estimate an expected size and expected location of an iris of an eye in the face in a frame of the series of frames and to determine a location of the iris by identifying a region within the expected location, a size of the region approximating the expected size, wherein pixels of the region have luminance values darker than pixels of all other regions in the expected location.

Furthermore, in accordance with some embodiments of the present invention, the camera and processor are incorporated into a handheld device.

Furthermore, in accordance with, some embodiments of the present invention, the processor is configured to apply a face detection algorithm to the frame.

Furthermore, in accordance with some embodiments of the present invention, the device further includes a display screen, wherein the processor is configured to modify an image displayed on the screen in accordance with a detected change in the determined location of the iris image.

Furthermore, in accordance with some embodiments of the present invention, the processor is configured to issue a signal of a change in a location of the region between a first frame of the series of frames and a second frame of the series of frames.

There is further provided, in accordance with some embodiments of the present invention, a method of tracking a movement of an eye, including: identifying in a first frame of a series of image frames a location of an area in a region of an eye in the first frame, the area including pixels having a darkest luminance measure in the region, the location relative to a reference area of a face in the first frame; identifying in a second frame of the series of image frames, a second location of an area in a region of the eye in the second frame, the area including pixels having a darkest luminance measure in the region, the location relative to a reference area of the face in the second frame; and comparing the location in the first frame to the second location in the second frame.

Furthermore, in accordance with some embodiments of the present invention, the method includes comparing a fit of a shape of a group of pixels within the area in the first frame, to a fit of the shape in the area in the second frame.

Furthermore, in accordance with some embodiments of the present invention, the method includes increasing a luminance value of a pixel in the area if the pixel has a chrominance value above a threshold level.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF THE INVENTION

Figure 1A:
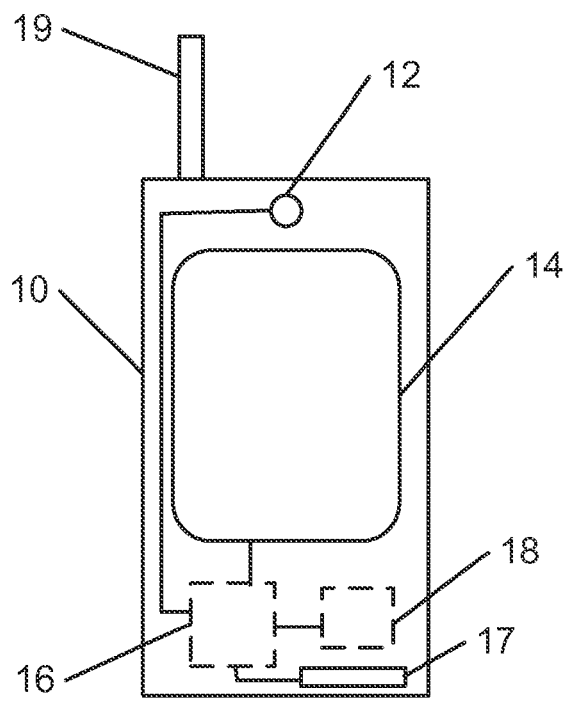
FIG. 1A is a schematic diagram of a device that may be configured for eye tracking, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

In accordance with embodiments of the present invention, eyes are tracked in an image of a face. For example, the image may include a video frame. The image may be acquired, for example, by a video camera that is aimed in the general direction of a face. A region of the face image that is expected to include the eye may be identified or estimated by application of a face detection algorithm, or may be estimated in accordance with previously acquired face images. Furthermore, an expected size of an iris of the eye may be estimated. The darkest part of the identified eye region of the face is detected. For example, a luminance measure for pixels in the region may be compared with similar luminance measures in other regions of the frame in the expected location. The detected darkest part, subject to further conditions as described below, is identified with, and assumed to represent, the iris and pupil of the eye. Thus, the position of the iris and pupil relative to the eye region or to the remainder of the eye is determined and tracked from frame to frame.

For example, the tracked location of the iris and pupil may be interpreted as representing a gaze direction. (An actual gaze direction may be determined from eye tracking after an appropriate initial calibration, e.g., by tracking the eye when a user is directed to look at a particular region of a display screen.) The resulting gaze direction may be utilized to control a device, such as selecting displayed content on a display screen. Eye tracking may be utilized, for example, to track of relative movement of the eye, to track an orientation and position of a head, or for determining or tracking a proximity from the camera.

In a typical application, a video camera that is used for eye tracking is incorporated in a handheld computer, smartphone, or similar device that includes a video camera and display screen. Such a device typically includes a camera (that may be operated to acquire still images or video frames, all such acquired images being herein referred to as frames) that faces the same side of the device as the display screen. Thus, a face of a user who is viewing the display screen of the device may be imaged by the camera of the device.

For example, a method of tracking a movement of an eye may include identifying in a first frame of a series of image frames a location of an area in a region of an eye. The area includes pixels having a darkest luminance measure in the region, the location being defined relative to a reference area of a face in the first frame. In a second frame of the series of image frames, a location of an area in a region of the eye is identified. The area includes pixels having a darkest luminance measure in that region. The second location is defined relative to a reference area of the face in the second frame. The location in the first frame is compared to the second location in the second frame. A fit of a shape of a group of pixels within the area in said first frame may be compared to a fit of the shape in the area in the second frame. The method may include increasing a luminance value of a pixel in a area if that pixel has a chrominance value above a threshold level.

FIG. 1A is a schematic diagram of a device that may be configured for eye tracking, in accordance with an embodiment of the present invention.

Device 10 may include a portable computing device, such as a handheld computer or smart phone. Device 10 includes a video camera 12.

Device 10 may include a motion sensor 17. Motion sensor 17 may include one or more sensors for measuring a change in velocity, rotation, or orientation of device 10. For example, motion sensor 17 may include an accelerometer, a gyroscope, compass, level, or other component capable of detecting a change in velocity or orientation of device 10.

Device 10 includes processor 16. Processor 16 may receive a video signal, or other video or image data from video camera 12. Processor 16 may operate in accordance with programmed instructions.

Programmed instructions for operation of processor 16 may be stored on data storage unit 18. Programmed instructions may include instructions for eye tracking in accordance with an embodiment of the present invention. Data storage unit 18 may include one or more fixed or removable, non-volatile or volatile, data storage units or computer-readable media that is capable of storing data for use by processor 16. Data storage unit 18 may be used to store, e.g., in the form of frames, video or image data that is acquired using video camera 12. Data storage unit 18 may be used to store data for use by processor 16 in displaying an image on display screen 14. Data storage unit 18 may be used to store one or more parameters for operation of processor 16, or one or more results of a calculation performed during operation of processor 18.

Processor 16 may control display of an image, e.g., of textual or graphical content, on display screen 14. For example, processor 16 may control scrolling, panning, or zooming of the displayed content. Processor 16 may be configured to modify displayed content on display screen 14 in accordance with a result of eye tracking.

Processor 16 may communicate with one or more external devices via a wired or wireless communications network. For example, a network connection, represented by antenna 19, may be utilized to receive from a remote device, or transmit to the remote device, data or instructions.

Processor 16 may be configured to issue a signal that indicates a change in a location of a position of a region (e.g., a position of an iris image) between one frame and another.

Figure 1B:
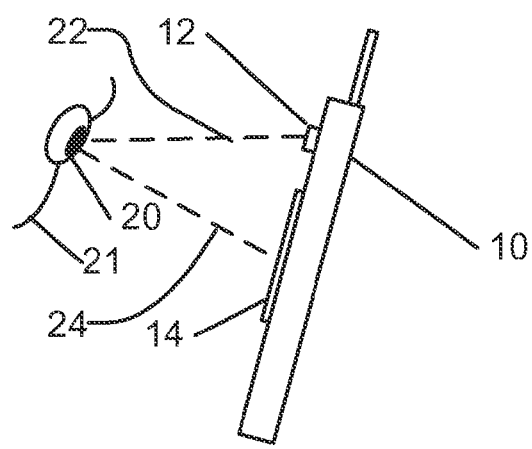
FIG. 1B schematically illustrates use of the device shown in FIG. 1A for eye tracking, in accordance with an embodiment of the present invention.

FIG. 1B schematically illustrates use of the device shown in FIG. 1A for eye tracking, in accordance with an embodiment of the present invention.

When used in eye tracking, device 10 may be oriented (e.g., by a user's hand) such that video camera 12 may face toward face 21 with iris 20. As described herein, a direction of line of sight 22 from video camera 12 to iris 20 may be determined. The determined line of sight 22 may be interpreted to determine a gaze direction 24 of iris 20.

A face may be detected in a frame by application of a face detection algorithm or object detection algorithm. For example, application of a real time face detection algorithm may include utilizing the Viola-Jones object detection algorithm (using Haar features), or various other face detection algorithms included in the Open Source Computer Vision Library (OpenCV) or elsewhere. Application of such a face detection or object detection algorithm may detect boundaries of a face in a frame (e.g., features of a face such as an eye strip, an eye region, a nose, or glasses). Application of the face or object detection algorithm may indicate boundaries (e.g., based on a known relationship among facial elements) of one or more regions of the face, such as an eye region. However, application of such a face or object detection algorithm alone may not be capable of efficiently and rapidly detecting the orientation of the eyes relative to the face or eye region with sufficient accuracy to enable tracking of eye movements.

In accordance with embodiments of the present invention, a region of the frame within an eye region of the previously identified face is found in which the pixels are darkest (least bright). For example, in some video frames, the darkest regions of an eye region of a face may be identified by identifying those regions of the face where the luminance (herein represented by Y) of the pixels is minimal. Equivalent measures of pixel brightness in other video representations or color spaces may be also used. The darkest region that is found may be assumed to represent the pupil and iris of an eye. The same darkest region may be identified and tracked in subsequently acquired frames.

Eye tracking in accordance with embodiments of the present invention may be advantageous. For example, identifying and following a darkest region of an eye area, may enable reliable tracking in a series of acquired frames, while making efficient use of processing resources.

In a typical healthy eye, the outer edge of the iris is of substantially fixed size, while the inner edge contracts or expands to decrease or increase the size of the pupil. Therefore, the region that includes both the iris and the pupil is tracked in accordance with embodiments of the present invention. However, a region smaller than the entire iris and pupil may be tracked (e.g., the size of a square region of pixels that is circumscribed by the iris image, other shapes or dimensions of pixel areas may be used). For simplicity, both the iris (the typically colored part of the eye) and the pupil it surrounds are herein referred to collectively as the iris.

In accordance with embodiments of the present invention, a dark region that represents the iris may be distinguished from another similarly dark or darker region (e.g., facial skin in deep shadow, glasses frame, eyebrow, facial hair) by its coloration (e.g., as defined by its chrominance values, its hue and saturation, its red-green-blue pixel values, or by its color as defined in another color space or colorimetric scheme). In some video frames, a pixel's color is characterized by red chrominance (herein represented by Cr) and blue chrominance (herein represented by Cb). Although examples of color definition using a Cr and Cb representation are described herein, other representations of pixel color may be used in other video representations or color spaces.

For example, in typical face images, facial skin is redder than the iris. (In some exceptional facial types or facial images, other criteria of eye tracking in accordance with embodiments of the present invention may be sufficient to distinguish an iris image from the remainder of the face image.) Thus, the color of a dark region may be examined, and if the pixels in the region are redder than a threshold value, those pixels may be eliminated from consideration as including the iris. For example, if Cr of a dark pixel, or group of dark pixels, exceeds a threshold value, it may be determined that the pixel is not a candidate for representing an image of the iris. Cb values, or a combination of Cr and Cb values, may also be examined, and compared with a threshold value or with a range of values, in order to eliminate a region from consideration as a candidate for representing an image of the iris (e.g., as likely to contain an image of skin or hair).

When it is determined that a pixel is not a candidate for representing an image of the iris, the pixel may be marked as such. For example, the pixel may be assigned Y value equal to a maximum Y value (e.g., Y=255 for an 8-bit representation), indicative of a maximally bright pixel. As another example, the Y value may be modified by addition of a value (e.g., determined as a function of Cr of the pixel) that indicates a likelihood or probability that the pixel represents an image of skin, rather than an iris. The size of the value added (e.g., 5, 10, 15 . . . ) may be selected to be indicative of the likelihood that the pixel does not represent an image of an iris.

Alternatively, the pixel may be indicated in another manner. For example, an array of values (e.g., true/false, or value between 0 and 1) that each correspond to one of the pixels may indicate whether or not the corresponding pixel is a candidate for representing an image of the iris, or a probability that the pixel represents an image of the iris.

A range of colors (e.g., Cr values) indicative of skin, or a probability that a particular color (e.g., Cr value) is indicative of skin, may be derived from the image itself. For example, a statistical analysis of pixel values (e.g., Cr) may be applied to the frame. A general knowledge of relative areas of different face features may be applied to the statistical analysis to distinguish one type of facial feature from another.

For example, a Cr value may be found for pixels that are known (e.g., from application of a face detection algorithm) to be outside the region of the face that contains the eyes (e.g., above the eye brows or below the bridge of the nose).

As another example, a user may calibrate or train an eye tracking application for a particular (e.g., the user's) face. Sample images may be acquired of facial skin (or other features of the face) and the iris in that face. Thus, various color thresholds may be determined for skin color and iris color of the face. Camera 12 may be aimed at the skin or eye from close range, or zoom may be controlled to reduce the field of view of camera 12 to be filled by the skin or eye. When calibrating, a user of device 10 may operate a control of device 10 to indicate an area of the face that is being imaged, or the user may be prompted (e.g., via display screen 14) to image a particular area of the face.

Application of eye tracking in accordance with an embodiment of the present invention may be expedited by attempting to minimize the region of the frame in which the darkest region is sought. For example, an initial approximate position of the eye may have been determined by application of the face detection algorithm. Searching for the iris may then be limited to that approximate position. Once the iris has been detected in one frame, the position of the iris in the next (or other subsequent) frame may be assumed to be nearby. Thus a search for the iris (darkest pixels) may begin at the previously determined position of the iris in the previously acquired frame. A starting position of a search for the iris may be based on an estimation of the position of the iris as determined in a previously or recently acquired frame. For example, the previously determined position may be adjusted based on motion of the iris in recently acquired frames, on detected motion of the video camera (e.g., as measured by motion sensor 17), or on a combination of these motions.

In this manner, eye tracking in accordance with embodiments of the present invention may avoid searching a wide area of the image. In addition, application of a face detection algorithm, which may require a relatively long amount of time or large amount of computation resources for running, need not be performed for each acquired frame.

An array of pixels (e.g. rectangular or otherwise shaped matrix of pixels forming a scan box) that is identified as representing an image of an iris may be characterized in a previously acquired frame by one or more representative values. Alternatively, the representative value may be derived from statistical analysis of a current frame, or from a combination of statistical analysis (e.g., histogram analysis) of current and previously acquired frames. For example, a representative value may include, or incorporate, a sum or average of a value of the pixels in the array (e.g., Y, Cr, Cb, or a function that is based on one or more of Y, Cr, and Cb), or a characterization of a range of pixel values in the array. Upon acquisition of a subsequent (e.g., next) frame, a new representative value may be evaluated for the corresponding scan box or array of pixels of the subsequently acquired frame. The new representative value (or values) of the corresponding pixel array may be compared to the original representative value (or values) that was evaluated for a previously acquired frame. For example, a difference between the representative values may be evaluated in light of one or more predetermined criteria. If the new representative value is evaluated to be different from the original representative value, then the corresponding pixel array of the subsequently acquired frame may be eliminated from consideration as representing an image of the iris. On the other hand, if the difference in the representative values is evaluated as being similar, then the corresponding pixel array of the subsequently acquired frame may be considered to be a candidate for representing an image of the iris.

The search for the iris may then continue by moving the scan box within the subsequently acquired frame to sequentially cover neighboring arrays of pixels. Moving the scan box includes evaluation of pixels in the scan box by for example calculation of the representative value (e.g., sum or average) for pixels covered by each position of the scan box in the subsequently acquired frame. The process of moving the scan box and evaluating pixels in the scan box may continue throughout a region of the image in which the iris may be expected to be found.

Failure to identify any candidate pixel array in the subsequently acquired frame may be understood to indicate a failure in tracking. For example, the subsequently acquired frame may have been acquired while the user was blinking, or device 10 may have been suddenly reoriented (e.g., turned), jerked, or dropped. In the event of failure to identify a candidate pixel array, additional regions (e.g., in addition to those regions of the frame which had been previously identified as representing the eyes) of the frame may be searched, or the face detection algorithm may be executed again. Failure to identify a candidate pixel array may also be understood as an indication that one or more criteria being used to characterize a candidate pixel array are not valid for the frame (e.g., significant change in illumination conditions). In such a case, a comparison of representative values may not be relevant, and searching for an iris image may continue without such a comparison.

In accordance with some embodiments of the present invention, identification of another (not iris) part of the face in an image may be utilized in selecting a region of the image in which to search for an iris. For example, an identifiable region of skin (e.g., high Cr or not dark) may be identified and a search area may be designated relative to the identified region. The region is a region of skin that may be expected to be imaged by video camera 12 together with the eyes. Such regions may include, for example, areas of facial skin below an eye or the nose (or between eyes when the user is not wearing glasses).

In order to search for a region of a frame that contains an iris image, characteristics of a region of pixels that potentially includes or that does not include an image of the iris may be defined. For example, potential iris image may be defined to include an expected number of pixels with a certain set of pixel properties (e.g., low Y or low Cr values). The expected number of pixels may be defined to a minimal value so as to include all expected appearances of the iris (e.g., to include a situation in which eye lids are almost shut and partially cover the iris). Limits regarding pixel brightness and color may be defined in terms of a context so as to accommodate variations in lighting conditions (e.g., brightness, color temperature, or spectrum). For example, a threshold value for a pixel property (e.g., Y, Cr, Cb, or a value is a function of one or more of Y, Cr, and Cb) may be defined in terms of a histogram (or other statistical) analysis of values for that pixel property in a frame. Threshold values for a subsequent frame (e.g. acquired under different illumination or camera settings) may be different. A histogram may be analyzed and the threshold value set for that frame in accordance with one or more statistical properties (e.g., range, average, median, standard deviation, or variance). For example, a threshold may be defined as a predefined percentage of the range (or part of a range) of values.

Pixels of the frame may then be scanned in terms of the threshold values in order to identify an iris. For example, region of pixels of fixed size (e.g., an expected size of an iris) may be analyzed and compared with another similarly sized region that is displaced from the first region.

Figure 2A:
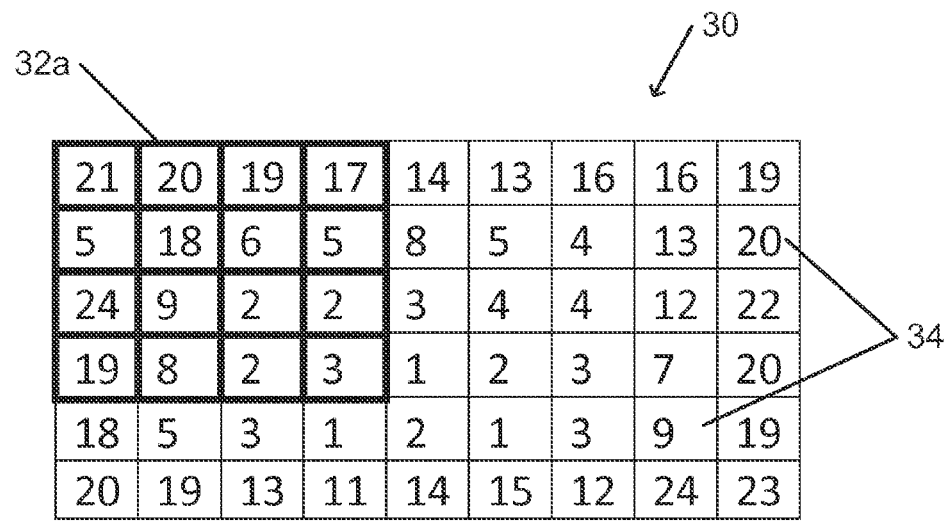
FIG. 2A schematically illustrates examination of pixels of an array of pixels of an image, as part of eye tracking in accordance with an embodiment of the present invention.

FIG. 2A schematically illustrates examination of pixels of an array of pixels of an image, as part of eye tracking in accordance with an embodiment of the present invention.

As shown, scan box 32a (4×4 pixels) of search window 30 of a frame is first analyzed. For example, the size of scan box 32a may correspond approximately to the expected size of an iris. The numbers in each pixel 34 represent the luminance of that pixel 34. For example, a sum or average of values of pixels 34 in scan box 32a may be calculated. As another example, the number of pixels 34 having a value that is less than a threshold value may be evaluated (for example, if the threshold value is defined to be 10, then scan box 32a contains 9 pixels 34 whose luminance values are below the threshold).

Figure 2B:
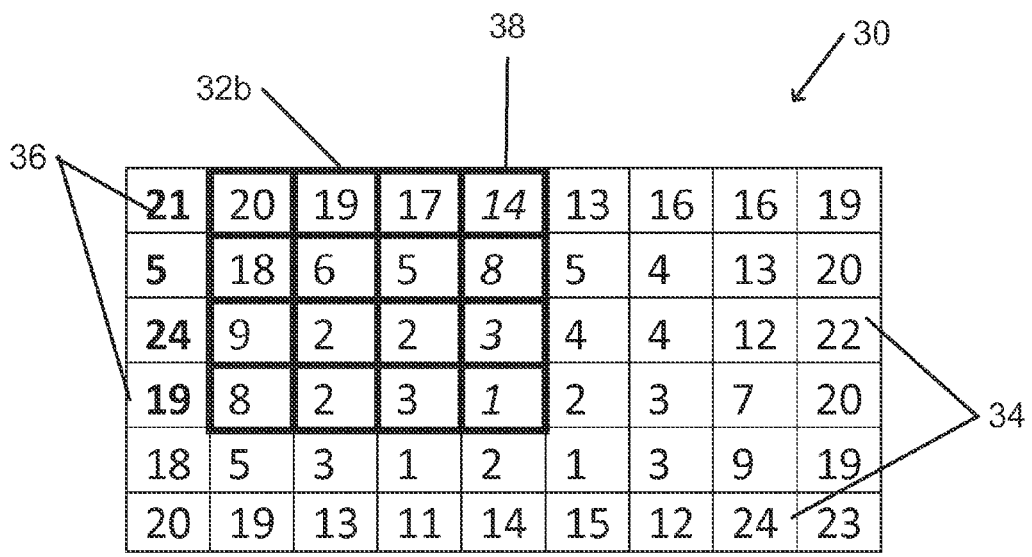
FIG. 2B schematically illustrates examination of other pixels of the array of pixels shown in FIG. 2A.

Another identically sized scan box of search window 30 may then be analyzed. FIG. 2B schematically illustrates examination of other pixels of the array of pixels shown in FIG. 2A. Scan box 32b is displaced by one pixel to the right of scan box 32a.

For example, the sum or average of pixels 34 within scan box 32b may be calculated, or a number of pixels 34 with value below threshold may be counted (e.g., with the same threshold of 10, scan box 32b of search window 30 includes 11 pixels 34 whose luminance values are below the threshold). When compared with scan box 32a, scan box 32b may be considered (subject to satisfaction of any other conditions) a more likely candidate for including an image of the iris than scan box 32a. (Visual examination of search window 30 would seem to indicate that the actual position of the iris image is below and to the right of scan box 32b).

In scanning a scan box over the frame (e.g., a 4×4 pixel region over search window 30), it may not be necessary to analyze every pixel of the scan box after it is moved. For example, as shown in FIG. 2B, pixels 36 (containing bold numbers) that were included in scan box 32a, are not included in scan box 32b. On the other hand, scan box 32b includes pixels in column 38 that were not included in scan box 32a. Thus, for example, a sum for scan box 32b may be calculated by adjusting a previously obtained sum for scan box 32a by deducting the values pixels 36 and adding the values of column 38. (The number of pixels below threshold in scan box 32b may be obtained by adjusting the number of pixels below threshold in scan box 32a, in the case shown, by deducting from 9 the single pixel of pixels 36 that is below threshold, and adding the additional 3 pixels in column 38 that are below threshold to obtain the result 11.)

The scanning process may be further shortened. For example, if a candidate pixel region is identified in a horizontal row (e.g., containing the most pixels in that row that meet criteria, e.g., maximum pixels with luminance below threshold), scanning in a vertical direction (e.g., downward) may commence from that identified pixel region. The vertical scanning may continue until analysis indicates that the current pixel region is unlikely to include an image of the iris (e.g., all pixels have luminance values that are greater than a threshold value).

Thus, a region may be identified (e.g., below the eye) that does not include an iris.

If a region with no iris image is identified, searching for the iris in the frame may be further facilitated. For example, if the region with no iris image is identified below the eye, searching for the iris image may take place above the identified region.

Values for pixels in the frame (e.g., luminance values) may be manipulated to facilitate identification of the iris image. For example, as described above, the luminance value of a pixel whose color is inconsistent with an iris image may be assigned a manipulated luminance value that is artificially increased (e.g., to a value indicative of saturation) so as to eliminate that pixel from consideration as a candidate for an iris image, or to reduce the contribution of that pixel in searching for the iris image. Such manipulation may enable correct identification of the iris, even when the iris is partially covered with a patch of bright glare, over an image of dark skin. Similar manipulation of pixel values may be based on a luminance threshold. For example, a pixel having a Y value that is above or below a range of values consistent with an iris image (e.g., as derived from analysis of a previously acquired frame) may be assigned a manipulated luminance value that excludes that pixel from consideration.

Figure 3A:
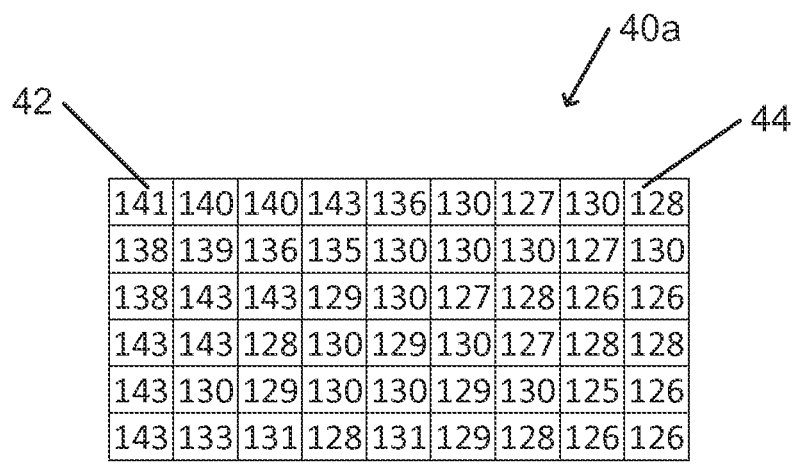
FIG. 3A schematically illustrates red chrominance (Cr) values for pixels of a frame.

FIG. 3A schematically illustrates red chrominance (Cr) values for pixels of a frame.

The Cr matrix 40a may be examined for Cr values that indicate that the pixel is unlikely to be part of an iris image. For example, a pixel with a Cr value above a threshold value (e.g., Cr>134), such as pixel 42, may be assumed to not represent a part of an iris image. On the other hand, a pixel with a lower Cr value, such as pixel 44, may be considered a candidate to be pixel of an iris image.

Figure 3B:
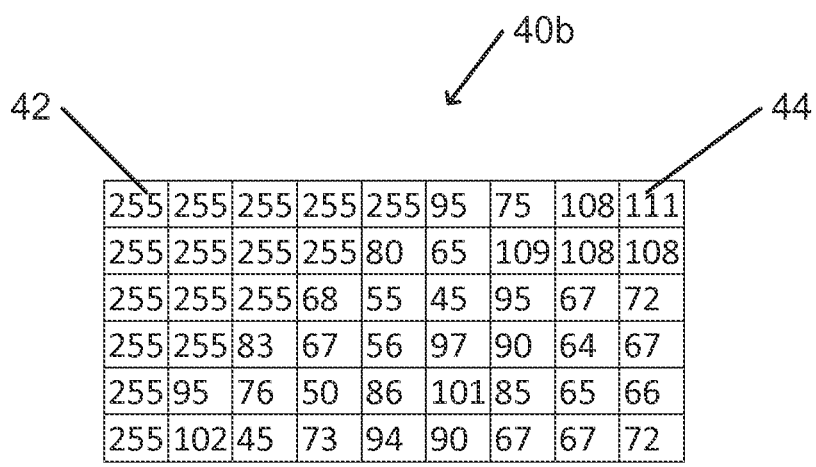
FIG. 3B schematically illustrates luminance (Y) values for the pixels shown in FIG. 3A after manipulation of the Y values in accordance with an embodiment of the present invention.

FIG. 3B schematically illustrates luminance (Y) values for the pixels shown in FIG. 3A after manipulation of the Y values in accordance with an embodiment of the present invention.

In manipulated Y matrix 40b, the Y values of the pixels have been adjusted in accordance with those pixels' Cr values. For example, the Y value of pixel 42, whose Cr value exceeds the Cr threshold value, is assigned a maximum (saturated) value of 255. On the other hand, the Y value of pixel 44, whose Cr value is below the threshold, remains unchanged from its value prior to manipulation (e.g., 111).

The scanning process for the iris image may be performed as described above (in connection with FIGS. 2A and 2B). For example, a lowest sum of Y values may be searched for by scanning a scan box in an eye region. The sum may be calculated for a scan box 32b by adding to a sum for a scan box 32a at a previous position newly added pixels in column 38, and subtracting values of pixels 36 that are no longer included in scan box 32b. At the end of scanning, the identified region (e.g., with lowest average value of manipulated pixel luminance) may represent the most likely position of the iris in the scanned region.

A value of a scan box (e.g., average or total pixel values within the scan box) may be evaluated and compared with an expected value or range of values (e.g., derived from analysis of one or more previously acquired frames). If the value of the scan box deviates from the expected value or range of values, then that scan box may be eliminated from consideration as covering an iris image.

Knowledge of the structure of the face and the position of a face image within a frame (either determined for a typical representative face, or previously determined for the face of a particular user) may be utilized to identify a region of the image in which the iris is likely to be found. Such knowledge may enable reducing a size of a region of the image in which the iris is sought.

For example, one or more rough templates containing a coarse array of cells (e.g., 3×3 or 6×4 or other dimensions) may be overlain on one or more corresponding regions of an identified face in a first frame N (=1). For example, characteristics of an initial rough template may be overlain after the irises are initially identified in frame N. For example, a region may correspond to an image of an area above an eye socket(s), a bridge of the nose, and/or a forehead.

Figure 4:
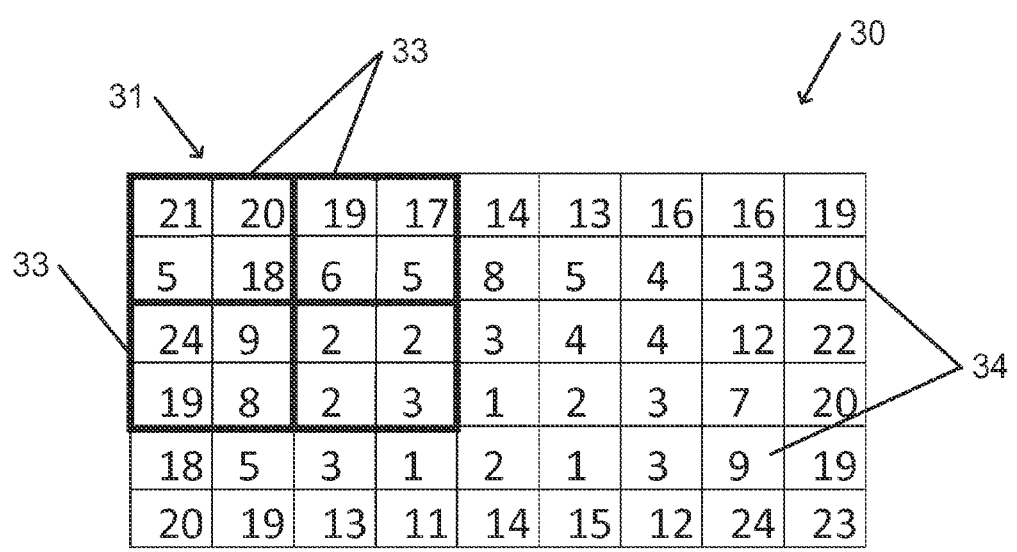
FIG. 4 illustrates rough template matching, in accordance with an embodiment of the present invention.

FIG. 4 schematically illustrates rough template matching, in accordance with an embodiment of the present invention. In the example shown, rough template 31 is divided into four cells 33.

A sum or average of values (e.g., Y) of pixels in each of the cells 33 of rough template 31 is calculated. (An average may be advantageous where the number of pixels of in each cell 33 is variable, e.g., as a result of changing the distance between the camera and the face.) In some cases, it may be advantageous to manipulate the pixel values in order to amplify differences during rough template matching. (For example, Y values may be squared or otherwise non-linearly manipulated.) The cell values for frame N may be stored as a template.

When a subsequent frame N+1 is acquired, a similar candidate template region (whose cell structure is identical to or approximates that of the rough template) of cells is initially overlaid on frame N+1 in the same position in which it was overlaid on frame N (or at another estimated corresponding position in frame N+1). Cell values are calculated for each of the cells in frame N+1 as they were for frame N. The position of the candidate template region relative to frame N+1 may be moved until the cell values in frame N+1 most closely correspond to the similar cell values in frame N. In calculating a value (e.g., a sum, for simplicity, with appropriate adjustment for an average or other quantity) for a cell after moving the candidate template region, a previous value for a cell may be adjusted by adding values of pixels that are newly included in that cell due to the moving, and subtracting values of pixels that are newly excluded from the cell (e.g., as described above with regard to scan regions pixels in connection with FIGS. 2A and 2B). For example, the position of the candidate template region in frame N+1 may be considered to most closely correspond to its position in frame N when the sum or average of absolute differences between cells in frame N and corresponding cells in frame $N_{+}1$ is minimized (with differences between such sums or averages possibly being amplified by non-linear manipulation as described above). (When the distance between the face and camera changes, the number of pixels in each cell may change. In this case, the cell value should include a pixel average rather than a pixel sum.) A search for the iris may then be executed in an eye region whose position is determined relative to one or more rough templates.

Thus, estimating the expected location in a frame includes comparing a value associated with a template of pixels in a prior frame to each of a plurality of values. Each of the values is associated with one of a plurality of templates of pixels in the frame. Estimating the expected location includes identifying a location in the frame of one of the templates whose associated value is closest to the value associated the template of pixels in the prior frame. Calculating the value associated with each template may include averaging or summing values of pixels in the template. The number of pixels in all of the templates is approximately equal.

In calculating the value, location of a template may be altered and the summation of values in cells of the template at the new location may be calculated by adding to the previous sum or average for each cell only values of pixels that are newly included in that cell as a result of altering the location, and deducting or eliminating from the sum or average only values of pixels that are excluded from that cell by giving effect to, or as a result of, altering the location (e.g., as discussed above in connection with FIGS. 2A and 2B).

Comparing values may include calculating a sum of absolute differences between the value associated with the template in the prior frame to each of the plurality of values. The various values may be non-linearly manipulated (e.g., squared) prior to summing.

A rough template determined in this manner (e.g., such that the rough template need only be sufficiently accurate to consistently cover the same region of a face image in different frames) may be relatively robust (e.g., stable in terms of consistently covering the same area of the face image) under changes in the face image over time from frame to frame (e.g., due to changes in lighting, face shape, face orientation, or face movement). This may facilitate searching for the iris image under such changes in conditions and creating an expected area wherein the iris is to be found or which may serve as a reference area or point relative to an expected location of the iris in a current or subsequent frame. The rough template may assist in minimizing the area that is searched for the iris images, and may enable tracking without interruption when the iris is covered or not visible (e.g., due to blinking or closing eyelids, or due to glare on glasses).

For example, rough template tracking may identify an area, such as a bridge of the nose, an eyebrow or group of freckles, having a group or cell of pixels that are particularly pronounced in a first frame. The pronounced or readily identifiable area may be in a known location relative to one or more irises. In a subsequent frame, pixel values (such as Y averages, Y sums or ranges or other measures) of the area may be compared to a series of similarly sized pixel areas in a face image to find the values of areas in the subsequent image that most closely match the value of the pronounced area in a prior or recent image. A closest match may be identified with the same pronounced area of the face as was identified in a prior image. The position of the pronounced area relative to the iris(es) in the current frame may be inferred or interpolated from their relative position in the prior frame. In some embodiments, the fixing of a location, characteristic, or identity of a rough template in a frame may be determined or fixed once a location of an iris is made.

In accordance with embodiments of the present invention, more than one previous rough template may be stored. Gradual changes may be expected from frame to frame. A search area in a newly acquired frame (e.g., frame N) may be checked for a match with a rough template for more than one previously acquired frame (e.g., ten previous frames, e.g., frames N−10, N−9 . . . N−1). For example, the rough template of a newly acquired frame may be compared with the average templates over two or more previous frames.

A difference may be calculated between a frame and one or more previously acquired frames. The difference may be compared to differences that are calculated between two previously acquired frames. For example, a difference between frame N and N−10 may be compared to the difference between frames N−9 and N−10. A difference between frames N and N−10 that is too large relative to the difference between frames N−9 and N−10, may be indicative of failure to properly track. Similarly, large changes in a Y value or Cr value of an area between two frames may be indicative that a reference area in a prior frame is not appropriate for identifying an object or area in a current frame.

The saving of rough templates for previous frames may be limited to cases where there is a significant difference between the rough templates. For example, the set of stored rough templates may be updated only when the rough template of the newly acquired frame has been detected to move by a minimal amount (e.g., by at least one pixel) relative to the last stored frame. Small changes of for example less than one pixel in position of a reference point or pronounced area of face may be indicative of slow series of movements, such that no updating of the rough template or reference area for rough template matching is called for. Such an updating would for example not detect a series of small movements in the face or eyes, since the movements of less than one pixel per frame would not be detected as movements when compared to an immediately preceding frame. A reference frame for comparing or determining motion may therefore be the most recent frame wherein a movement of at least one pixel was detected.

A rough template is usually renewed based on the last best match. Thus, a search area in frame N may be matched to a template representing the best match in frame N−1. For example, when the image in the frame has moved by a distance less than one pixel, then the best match in frame N is in the same position as in frame N−1, even though the values have changed (since there was some motion). The values of the new best match (from frame N) are used as the rough template for scanning frame N+1. In frame N+1, the motion may also be small so again there is a change in values but the position of best match has not changed as compared with the updated rough template from frame N. (If frame N+1 were scanned using the template from frame N−1, then the position of the best match would have changed enough to represent a full pixel movement.) Therefore, in order to correctly update the position of the rough templated, when there is no change in position and the best match in frame N is exactly where it was in frame N−1, frame N+1 is then compared with the rough template of frame N−1 (rather than to the rough template of frame N). This process continues for subsequently acquired frames (frame N+2 and onward) until a best match occurs in a different position than in frame N−1. At this point, values of the rough template at that new position values will be used as a rough template for subsequent frames.

In accordance with embodiments of the present invention, when comparing two templates, differences between one corresponding pair of cells in the two templates may be given greater weight than differences between other pairs of cells. Similarly, a subregion of one of the cells may be emphasized over another portion of that cell.

For example, in calculating a sum of absolute differences between corresponding cells, the sum may be a weighted sum. Consider a rough template of cells indexed by i. An absolute difference $D_i$ is calculated for each pair of corresponding cells i of the template as applied to two acquired frames (or an acquired frame and an average of other acquired frames). In calculating a sum S that is to be minimized, each absolute difference $D_i$ may be multiplied by a corresponding weighting factor $a_i$. The size of the weighting factor $a_i$ determines the relative importance of the corresponding difference $D_i$ in determining the correct position of the template in a newly acquired frame. (A weighting factor with a fractional value between 0 and 1 may be applied to deemphasize a cell difference.) Thus, sum S may be calculated as $S=a_1 \cdot D_1+a_2 \cdot D_2+ \ldots$ The weighting factors may be based on known structure and nature of the face. For example, if it is known that an image of the edge of the face generally includes some of a background, or that a section of the image (e.g., the nose) tends to be move relative to the rest of the face image due to small changes in camera angle, that region of the image may be assigned a low weighting factor. Similarly, a region near the eyes, as may be determined from for example face detection function or from for example an area of a current frame that corresponds to an eye region as is known from a prior frame, may be assigned a greater weighting factor.

Assignment of weighting factors may be based on analysis of the cells of the rough template when it is created. For example, those cells having higher contrast with much lower or higher Y values than other cells, may thus stand out relative to neighboring cells, and may be assigned a greater weighting factor than other cells that may be more less pronounced or difficult to find or identify in subsequent frames.

Weighting factors may be modified during the course of eye tracking. For example, a change in angle of the face (e.g., derived from a change in position of the rough template, the iris image, or any other tracked element of the previous frame) that brings a cell close to an edge of the image (such that part of background image is included in the cell such that calculations with respect to that cell may be misleading) may cause the weight of that cell to be reduced, as it may be assumed that the edge cells will be harder to identify and find in subsequent frames.

Similar weighting factors may be applied in calculating an average value (e.g., average luminance) for various subregions of a single cell. Similarly, in calculating sum S, outlying differences may be ignored or deemphasized.

For example, various subregions of a region (e.g., cell or scan box) may be weighted by defining a focus measure. When defining a focus measure, a focus box of pixels is defined within a cell or scan box to indicate pixels that are to be assigned a greater weight. An additional level of smaller focus boxes may be defined within a larger focus box. When calculating an average value (e.g., of Y, Cr, or Cb), separate averages are calculated for each box. The average value for a larger box is calculated by averaging the average values for the larger box, and for each smaller box contained within the larger box. Thus, the pixels within a focus box that are to be given larger weight are counted more often in calculating the average than pixels that are not included within the focus box.

As another example of utilizing knowledge of structure of the face, if one iris is detected, a position of the other iris may be estimated.

For example, it may be known that the eyes are expected to be found at a particular displacement (distance and direction) relative to the identified region of skin. The displacement on the face may be converted to a displacement in pixels in an acquired frame. For example, a scaling factor for converting a distance between facial features and a distance between pixels that represent those features may be determined from identified features in the acquired frame or from a sensed or otherwise determined distance between the camera 12 and face 21. Similarly, an orientation of an acquired frame relative to face 21 may be derived from an orientation of a feature of the image (e.g., of a line connecting the eyes).

In accordance with embodiments of the present invention, detection of the iris may include comparison of a detected dark region in an image with an expected size of the iris. For example, a typical maximum size of the iris may be known relative to one or more other sizes of features of the face (e.g., boundaries of the face), or to one or more distances between detectable features of the face (e.g., between eyes, or between other features of the face that are sufficiently close to the iris so as to be imaged together with the iris). Such features may be detected, e.g., by application of the face detection algorithm. Alternatively, an acquired image of the face of a particular user may be analyzed to determine relative sizes and distances in the face of that user. Comparison of the size of a detected region to another size or distance related to features of the face (rather than to an absolute distance, e.g., in pixels or other length units) eliminates effects of varying distance between camera 12 and iris 20 on the apparent size of the iris image. In this manner, a detected iris image that is too large (e.g., having a lateral dimension whose ratio to another detected feature size or distance is larger than expected) may be eliminated from consideration.

For example, a distance between eyes that is measured in one frame after the iris is detected may be used to estimate an expected size of an iris image in a following frame. At the beginning of eye tracking, application of the face detection application may yield a (less accurate) estimate of iris size, or an eye detection algorithm (similar to face detection) may be applied to obtain a general position of the eye and measure the distance between eyes. Once the iris image is detected in the image in accordance with an embodiment of this invention, its diameter may be measured and compared to the distance between eyes to obtain a ratio for a particular user. In subsequently acquired frames, the distance between eyes as measured in pixels is obtained. The measured distance may be compared to the previously measured distance, and the expected iris size may be estimated or adjusted based on the ratio of distance between the eyes in such subsequent frame to iris size. Alternatively, an average ratio (e.g., for all people, or for a particular population) may be used to estimate the iris size.

A measured distance in pixels between the eyes may be further utilized to calculate a distance between the camera and the eyes. Thus, a three-dimensional location or location of the iris in space relative to the camera may be determined.

On the other hand, a lateral dimension of a detected dark region that represents an iris may sometimes be expected to be smaller than an expected size, e.g., when the eyelids are partially closed. After iris detection, the image may be scanned above and below the detected iris image to locate the edges of the eyelids. The height or other dimensions of the iris image that results may be utilized to predict a height, shape or other dimensions of the iris image (e.g., a rectangular region that may result from eyelids that partially occlude an iris) in a following frame. Such expected shape or dimensions of the iris may be altered within a series of frames by for example detection of edges of the iris, changes in a location of edges of the iris or changes in a size of the iris. Some of such changes may indicate for example that an eyelid is opening, closing or otherwise changing its occlusion of an area or region of an iris.

In accordance with some embodiments of the present invention, a distance between the tracked eyes (which may be interpreted to estimate a distance between the camera and the eyes) may be used to track the relative position in three-dimensional space of the eyes and the head containing them. An orientation (e.g., angle to the horizontal or vertical) of a line that connects the detected iris between the eyes may be used to define an orientation of the head relative to the camera. An average of changes in position of each eye may be utilized to increase the accuracy and stability of an estimate of head position or orientation.

When one eye is covered or otherwise not visible in an acquired frame, eye tracking may continue take place based on the one visible eye, e.g., until the non-visible eye is again imaged.

A result of eye tracking as described above may be as a basis for higher resolution tracking and tracking of increased accuracy. For example, after a darkest region is identified, a location of a center of the iris image may be calculated. Three or four edges of the iris image may be located (e.g., by application of an edge detection algorithm) to define an appropriate circular or oval shape, and the location of the center of the defined shape may be calculated. Interpolation (e.g., bilinear or bi-cubic) may be utilized to increase the accuracy of locating the edges. Thus, since finding the iris image by locating the darkest area of pixels yields a fast, stable, and robust indication of the location of the iris image, an interpolation among only a few pixels may yield an accurate location of the center of the iris with minimal calculation.

In some embodiments it may not be necessary to find a center of an iris. Rather, dimensions of a square, rectangle or random shape may be fitted into an area of an iris that is detected in a frame, and a comparison may be made of a fit of such shape into an iris area in a subsequent frame. A change in the fit, the location of the fit or in a shape that fits into the area may indicate a change in a location of an iris.

Knowledge of possible eye movements may be utilized as a criterion in eliminating some errors in eye tracking, in accordance with some embodiments of the present invention. For example, unrelated movement of the eyes (e.g., in a face that has not been identified as having eye movement anomalies) may be interpreted as an indication of a false or erroneous detection of at least one of the irises.

Concurrent failure to identify both irises may be interpreted as indicating blinking. In such a case, the frame or frames in which no irises were detected (e.g., within a time limit that is typical of a blink) may be ignored, and tracking may be resumed from a position based on rough template tracking (which continues even when the iris is not visible), or on the last detected iris position after the eyes are reopened.

Figure 5:
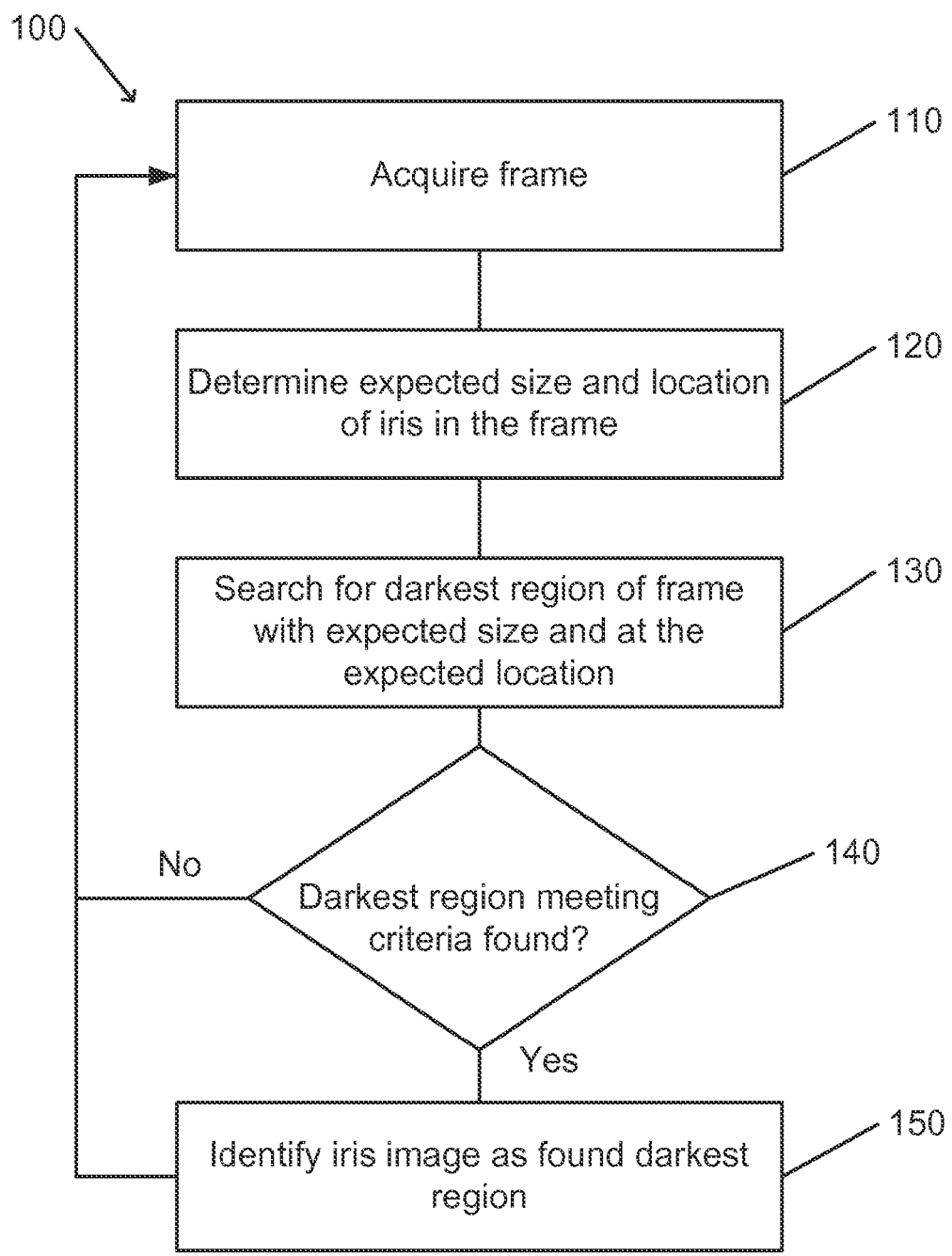
FIG. 5 is a flowchart depicting a method for eye tracking in accordance with an embodiment of the present invention.

In accordance with embodiments of the present invention, a method for eye tracking may be executed. FIG. 5 is a flowchart depicting a method for eye tracking in accordance with an embodiment of the present invention.

It should be understood with respect to the flowchart, that the division of the illustrated method into separate operations represented by blocks of the flowchart has been selected for convenience only. Alternative division of the depicted method into discrete operations is possible with equivalent results. Such alternative division of the depicted method into discrete operations should be understood as representing embodiments of the present invention.

Furthermore, it should be understood that unless indicated otherwise, that the illustrated order of operations of the depicted method as represented by the positions of the blocks in the flowchart has been selected for convenience only. Execution of the illustrated operations in alternative order, or concurrent execution of operations of the depicted method, is possible with equivalent results. Any such reordering of operations of the depicted method should be understood as representing an embodiment of the present invention.

Eye tracking method 100 may be executed by a processor that is configured to receive images from a video camera, or from another device (e.g., data storage device or data buffer) that provides video frames or a series of images of a face. The processor may be incorporated into a device (e.g., handheld computer, smartphone, or portable phone) that includes the camera, or a processor that is in communication with a device that includes the camera.

A frame that is expected to include an image of a face may be acquired (block 110). Typically, the acquired frame is one of a sequence of acquired frames. The frame may be acquired directly from a digital video camera, may be retrieved from a storage device of buffer, or may be derived from an analog video frame sequence using frame grabber technology.

An expected location of an iris image (or of an eye image) within the frame, and an expected size of the iris image, may be determined (block 120).

For example, if the frame is an initial frame, or if the frame was acquired after it had been previously determined that the eye tracking had failed (e.g., after a sufficiently long, in accordance with predetermined criteria, series of frames in which no iris image was identifiable), a face detection algorithm may be applied. The face detection algorithm may designate a region of the frame as containing an image of the eye.

As another example, if an iris image had been previously identified in a previously acquired frame, an expected location in the current frame may be based on the location of the previously identified iris image.

An initial position of the expected location may be calculated by displacing the previous location by displacement calculated on the basis of detected motion of the iris image (e.g., derived from analysis of previous frames) or of the camera (e.g. by motion detectors).

Determining an expected location may include identifying a region of the face image that is likely to be at a known position relative to the iris image. For example, regions of the image may be matched to a rough template to locate one or more characterized regions of the face image. An eye region of the image in which the iris is expected to be found may be known relative to the positions of one or more rough templates. (As another example, e.g., when insufficient processing power is available for rough template matching, a patch of skin below an eye, above an eye, or between the eyes may be identified.) Such a region may be identified, e.g., by comparing sequentially various cells of a candidate match to the rough template that is placed at various locations within a search window of the frame to the rough template. The location where the best match is obtained is identified as the rough template in that frame.

An expected size of the iris may be determined relative to a size of another feature of the face image. For example, a distance between the eyes may be calculated, or initially calculated, as a result of application of the face detection algorithm, or from previously identified iris images in a previously acquired frame. An expected maximum size of the iris image, or an expected dimension (e.g., horizontal width) of the iris image, may be derived from a previously determined ratio of feature sizes in the face being imaged, or in another face image (e.g., a standard face image, or one of a set of standard face images).

A region of the frame that is located within the confines of the expected location, whose size is consistent with the expected size, and that includes the darkest pixels is searched for (block 130).

For example, the darkness of the pixels may be determined by their luminance values. Darkness of the pixels may be determined by their adjusted luminance values, in which the luminance values are manipulated in accordance with their color. For example, luminance values may be adjusted by increasing the luminance value of any pixel whose color is not indicative of that pixel being part of an iris image. The darkest region may be found, for example, by sequentially locating and evaluating pixels within a rectangle or other shape of pixels (whose size approximates an expected size of the iris) that is placed at locations in a search window of the frame. Evaluation of the pixels may include calculating a quantity or measure, such as the sum, range or average of pixel values, such as luminance values or adjusted luminance values.

An identified dark region may be considered to have a size that is consistent with the expected size when the size of the identified region is no larger than the expected size. On the other hand, a size of the identified region that is smaller than the expected size may be considered to have a size that is consistent with the expected size. For example, the iris image may be small due to eyelids being partially closed.

If such a darkest region meeting the criteria (e.g., having a suitable color and size, and located at a suitable location) is found (block 140), then the found darkest region may be identified as an image of the iris (block 150). The process of acquiring a frame and identifying an iris image within the frame may be repeated for successive frames (repeating the operations of blocks 110 through 150). A change in iris location may be utilized in operation of a device or otherwise (e.g., for research purposes). For example, the location of the iris image may be interpreted to determine a gaze direction. The gaze direction may be utilized as user input in controlling operation of a device or software application (e.g., in scrolling displayed text or panning a displayed image).

If no darkest region meeting appropriate criteria (e.g. whose size, color, average pixel value or other characteristic value is not consistent with an expected range of values based on previously acquired frames or other criteria) is found within the expected location, execution of eye tracking method 100 may continue with acquisition of another frame (repeating the operations of blocks 110 through 150). Failure to identify an iris in a series of successively acquired frames may result in resetting or restarting execution of eye tracking method 100 (e.g., application of a face detection algorithm to an acquired frame). For example, if a comparison between a rough template match for the current frame and a rough template for a previous frame show an inconsistency, then the face detection algorithm may be reapplied.

The invention claimed is:

1. An eye tracking method, comprising:
   acquiring a series of video frames comprising face images, using a video camera of a handheld portable computing device,
   in a first frame of the series of acquired frames, estimating an expected size and expected location of an image of an iris of an eye within said first frame;
   determining a first location of the iris image within said first frame by identifying a first region within the expected location, a size of the first region being consistent with said expected size, wherein a first sum luminance value of pixels of said first region is darker than a sum luminance value of pixels of other regions of the same size as the first region, within said expected location;
   determining a second location of the iris image within a second frame by identifying a second region within the expected location, a size of the second region being consistent with said expected size, wherein a second sum luminance value of pixels of said second region is darker than a sum luminance value of pixels of other regions of the same size as the second region, within said expected location;
   measuring change in location of the second identified region with respect to the location of the first identified region; and
   determining the movement of the iris based on the change in the measured location.

2. The method of claim 1, wherein estimating the expected size and the expected location comprises applying a face detection algorithm to the frame.

3. The method of claim 1, wherein estimating the expected location comprises comparing a value associated with a template of pixels in a prior frame to each of a plurality of values, each of said plurality of values associated with a template of a plurality of templates of pixels in said frame, and identifying a location in said frame of a template of said plurality of templates whose associated value is closest to said value associated with said template of pixels in said prior frame.

4. The method as in claim 3, wherein said comparing comprises calculating said value for said template of said plurality of templates by summing values of pixels in said template of said plurality of templates, said template of said plurality of templates including a number of pixels approximating a number of pixels in said template of pixels in said prior frame.

5. The method of claim 4, comprising applying a non-linear manipulation to said values of pixels in said template of said plurality of templates by a pre-defined factor.

6. The method as in claim 3, comprising altering a location of said template of said plurality of templates, and adding to said summing only values of pixels included in said template by giving effect to said altering, and eliminating from said summing only values of pixels excluded from said template by giving effect to said altering.

7. The method of claim 3, wherein said comparing comprises calculating a sum of absolute differences between said value associated with said template of pixels in said prior frame to each of said plurality of values.

8. The method of claim 1, wherein said estimating said expected size comprises comparing a distance in pixels between eyes of a face in said frame to a distance in pixels between eyes in a prior frame of said series of frames, and changing said size relative to a change in said distances.

9. The method of claim 1, comprising increasing a luminance value of pixels in said expected location if said pixels have chrominance values above a threshold level.

10. The method as in claim 1, further comprising:
    deriving, from at least one pixel, a color indicative of facial skin; and
    increasing luminance value of pixels having indication of facial skin.

11. The method as in claim 10, wherein the indication of facial skin is based on a predetermined threshold.

12. The method as in claim 1, wherein said handheld portable computing device is one of handheld computer, smartphone, or portable phone.

13. The device of claim 1, wherein said expected size of the iris image is determined relative to a size of another feature of the face image.

14. An eye tracking device comprising:
    a video camera for a handheld portable computing device, said video camera configured to capture an image of a face in each frame of a series of frames; and
    a processor configured to:
        estimate an expected size and expected location of an image of an iris of an eye in said face in a first frame of said series of frames,
        determine a first location of said iris within the first frame by identifying a first region within said expected location, a size of the first region approximating said expected size, wherein a first sum luminance value of pixels of said first region is darker than a sum luminance value of pixels of other regions of the same size as the first region, within said expected location;
        determine a second location of the iris within a second frame by identifying a second region within the expected location, a size of the second region approximating with said expected size, wherein a second sum luminance value of pixels of said second region is darker than a sum luminance value of pixels of other regions of the same size as the second region, within said expected location;
        measure change in location of the second identified region with respect to the location of the first identified region; and
        determine the movement of the iris based on the change in the measured location.

15. The device of claim 14, wherein the processor is configured to apply a face detection algorithm to the frame.

16. The device of claim 14, further comprising a display screen, wherein the processor is configured to modify an image displayed on the screen in accordance with a detected change in the determined location of the iris image.

17. The device as in claim 14, wherein said processor is configured to issue a signal of a change in a location of said region between a first frame of said series of frames and a second frame of said series of frames.

18. The device of claim 14, wherein said handheld portable computing device is one of handheld computer, smartphone, or portable phone.

* * * * *